(12) United States Patent
Maitland et al.

(10) Patent No.: US 11,576,679 B2
(45) Date of Patent: Feb. 14, 2023

(54) HEATED ENDOVASCULAR CATHETER INJECTION DEVICE

(71) Applicant: The Texas A&M University System, College Station, TX (US)

(72) Inventors: Duncan J. Maitland, College Station, TX (US); Mark A. Wierzbicki, College Station, TX (US); Landon D. Nash, College Station, TX (US); Wonjun Hwang, College Station, TX (US)

(73) Assignee: The Texas A&M University System, College Station, TX (US)

( * ) Notice: Subject to any disclaimer, the term of this patent is extended or adjusted under 35 U.S.C. 154(b) by 1059 days.

(21) Appl. No.: 16/319,931

(22) PCT Filed: Jul. 28, 2017

(86) PCT No.: PCT/US2017/044284
§ 371 (c)(1),
(2) Date: Jan. 23, 2019

(87) PCT Pub. No.: WO2018/022954
PCT Pub. Date: Feb. 1, 2018

(65) Prior Publication Data
US 2019/0231362 A1 Aug. 1, 2019

Related U.S. Application Data

(60) Provisional application No. 62/368,350, filed on Jul. 29, 2016.

(51) Int. Cl.
*A61B 17/12* (2006.01)
*A61B 90/00* (2016.01)
(Continued)

(52) U.S. Cl.
CPC .. *A61B 17/12195* (2013.01); *A61B 17/12113* (2013.01); *A61B 17/12181* (2013.01);
(Continued)

(58) Field of Classification Search
CPC ........ A61B 17/12195; A61B 17/12113; A61B 17/12186; A61B 90/39;
(Continued)

(56) References Cited

U.S. PATENT DOCUMENTS 4,170,997 A 10/1979 Pinnow et al.
5,005,180 A 4/1991 Edelman et al.
(Continued)

OTHER PUBLICATIONS

The International Searching Authority, Written Opinion of the International Searching Authority and the International Search Report dated Jan. 9, 2018 in International Application No. PCT/US17/44284, eight pages.

(Continued)

*Primary Examiner* — Anh T Dang
(74) *Attorney, Agent, or Firm* — Trop, Pruner & Hu, P.C.

(57) ABSTRACT

An embodiment includes a system comprising: a catheter; an optic fiber having a long axis and a short axis that is orthogonal to the long axis; first and second radiopaque elements coupled to the optic fiber; a first wire coupled to the optic fiber and extending from the first radiopaque element to the second radiopaque element; a fluid; wherein (a)(i) the first wire wraps at least partially around an exterior surface of the optic fiber; (a)(ii) an outer diameter of the first wire and an outer diameter of the optic fiber are collectively less than an inner diameter of the catheter, and (a)(iii) the first wire is configured to center the optic fiber within the catheter within a plane orthogonal to the long axis.

20 Claims, 10 Drawing Sheets

(51) Int. Cl.
*A61M 29/00* (2006.01)
*A61B 17/00* (2006.01)

(52) U.S. Cl.
CPC ........ *A61B 17/12186* (2013.01); *A61B 90/39* (2016.02); *A61M 29/00* (2013.01); *A61B 2017/00092* (2013.01); *A61B 2017/00867* (2013.01); *A61B 2017/00871* (2013.01); *A61B 2017/12068* (2013.01); *A61B 2017/12072* (2013.01); *A61B 2090/3966* (2016.02)

(58) Field of Classification Search
CPC ........... A61B 2017/00092; A61B 2017/00867; A61B 2017/00871; A61B 2017/12072; A61B 2090/3966
See application file for complete search history.

(56) References Cited

U.S. PATENT DOCUMENTS

| | | | | |
|---|---|---|---|---|
| 6,547,779 | B2* | 4/2003 | Levine | A61B 18/26 606/7 |
| 9,526,505 | B2* | 12/2016 | Marks | A61B 17/12145 |
| 2002/0095169 | A1 | 7/2002 | Maitland et al. | |
| 2003/0236533 | A1 | 12/2003 | Wilson et al. | |
| 2012/0158034 | A1* | 6/2012 | Wilson | A61B 17/12145 606/191 |
| 2013/0253634 | A1* | 9/2013 | Wilson | A61F 2/82 623/1.19 |
| 2015/0257764 | A1 | 9/2015 | Wilson et al. | |

OTHER PUBLICATIONS

Hearon, et al. "A Processable Shape Memory Polymer System for Biomedical Applications", Advanced Healthcare Materials, 2015, 13 pages, Wiley-VCH Verlag GmbH & Co. KGaA, Weinheim, Germany.

Nash, et al., "Characterization of Plasma Deposited Hydrocarbon Diffusion Barriers for Embolic Foam Devices", Proceedings of the 9th IEEE International Conference on Nano/Molecular Medicine and Engineering, Nov. 15-18, 2015, six pages, Institute of Electrical and Electronics Engineers, Hawaii, U.S.

Maitland, et al. "Photothermal Properties of Shape Memory Polymer Micro-Actuators for Treating Stroke", Lasers in Surgery and Medicine, 2002, 11 pages, vol. 30, Wiley-Liss, Inc.

Maitland, et al., "Prototype laser-activated shape memory polymer foam device for embolic treatment of aneurysms", Journal of Biomedical Optics, May/Jun. 2007, three pages, vol. 12, Issue 3.

Boyle, et al., "In vitro and in vivo evaluation of a shape memory polymer foam-over-wire embolization device delivered in saccular aneurysm models", Journal of Biomedical Materials Research B: Applied Biomaterials, 2015, pp. 1-9, vol. 8, Wiley Periodicals, Inc.

* cited by examiner

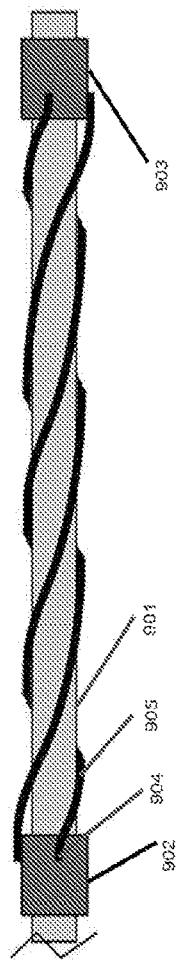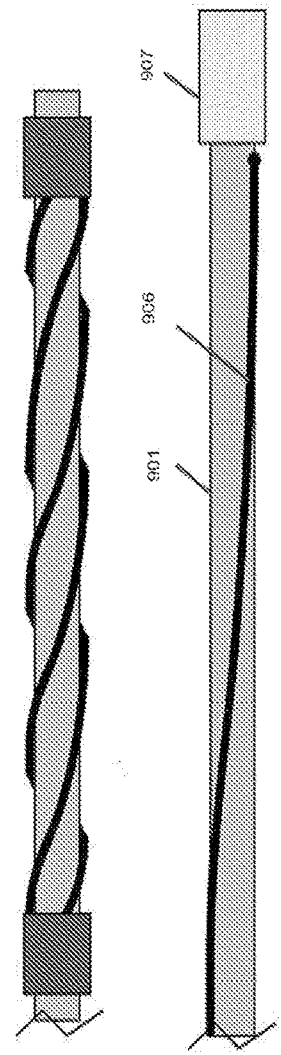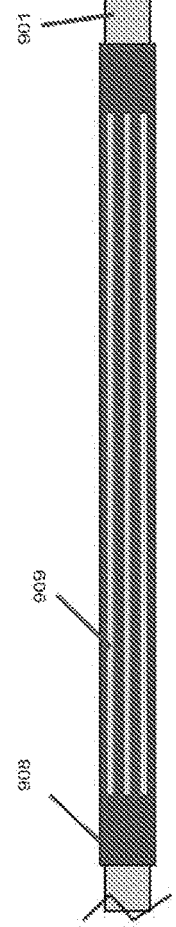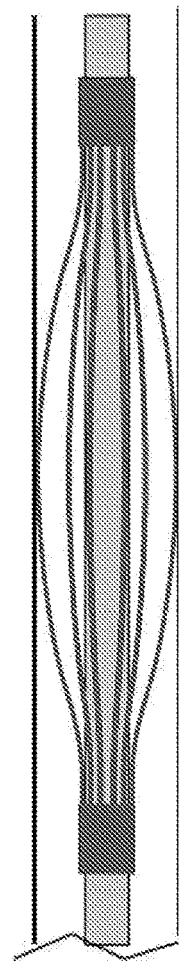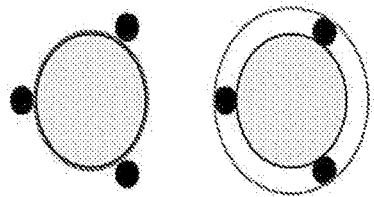
FIGURE 9A Centering Method 1
FIGURE 9B Centering Method 2
FIGURE 9C Thermocouple placed proximally with polymer tip
FIGURE 9D Thermocouple placed distally with cleaved optical fiber tip
FIGURE 9E Centering Method 3: Nitinol Constrained
FIGURE 9F Centering Method 3: Nitinol expanded, contacting catheter wall

HEATED ENDOVASCULAR CATHETER INJECTION DEVICE

CROSS-REFERENCE TO RELATED APPLICATION

This application claims priority to U.S. Provisional Patent Application No. 62/368,350 filed on Jul. 29, 2016 and entitled "HEATED ENDOVASCULAR CATHETER INJECTION DEVICE", the content of which is hereby incorporated by reference.

STATEMENT REGARDING FEDERALLY-SPONSORED RESEARCH OR DEVELOPMENT

This invention was made with government support under National Institute of Biomedical Imaging and Bioengineering Grant No. RO1EB000462 and DEP Shape Memory Therapeutics, Inc. Grant No. C13-00543. The government has certain rights in the invention.

BACKGROUND

Current endovascular therapies for intracranial saccular aneurysms result in high recurrence rates due to poor tissue healing, coil compaction, and aneurysm growth. Intracranial saccular aneurysms typically develop at the apex of subarachnoid arterial bifurcations at the base of the brain. Subarachnoid hemorrhage, primarily caused by ruptured intracranial aneurysms, affects approximately 1 in 10,000 Americans each year and is fatal in 35% to 50% of all patients.

Standard endovascular treatment using bare metal coils involves delivering several platinum wire coils through a microcatheter into an aneurysm to occlude the aneurysm volume. The treatment goal is for the packed coils to provide sufficient flow stasis to result in embolization of the aneurysm sac and neointima growth across the aneurysm neck. However, implanted bare platinum coils are prone to compaction, result in low volume occlusion ranging from 23-37%, and exhibit a recanalization rate of 21-34% with 13% requiring retreatment. Minimal tissue response to the bioinert platinum coils stunts tissue healing, resulting in unorganized thrombus formation within the aneurysm sac that may not organize within 3 years following treatment. Several devices, including polymer embedded coils, have been investigated in order to improve upon bare platinum coiling outcomes. Bioactive and biodegradable polymer coated coils increase tissue response, but are susceptible to recanalization as the polymer is absorbed. HydroCoils®, coils coated with hydrogel that swells in water, have shown to improve volume occlusion to 45-73%. Although major recurrence has been reported to be lower when using HydroCoils®, the effect on long-term clinical outcomes is unclear.

BRIEF DESCRIPTION OF THE DRAWINGS

Features and advantages of embodiments of the present invention will become apparent from the appended claims, the following detailed description of one or more example embodiments, and the corresponding figures. Where considered appropriate, reference labels have been repeated among the figures to indicate corresponding or analogous elements.

FIGS. 9(A)-(F) include differing embodiments of a laser heated actuation system.

DETAILED DESCRIPTION

Figure 1:
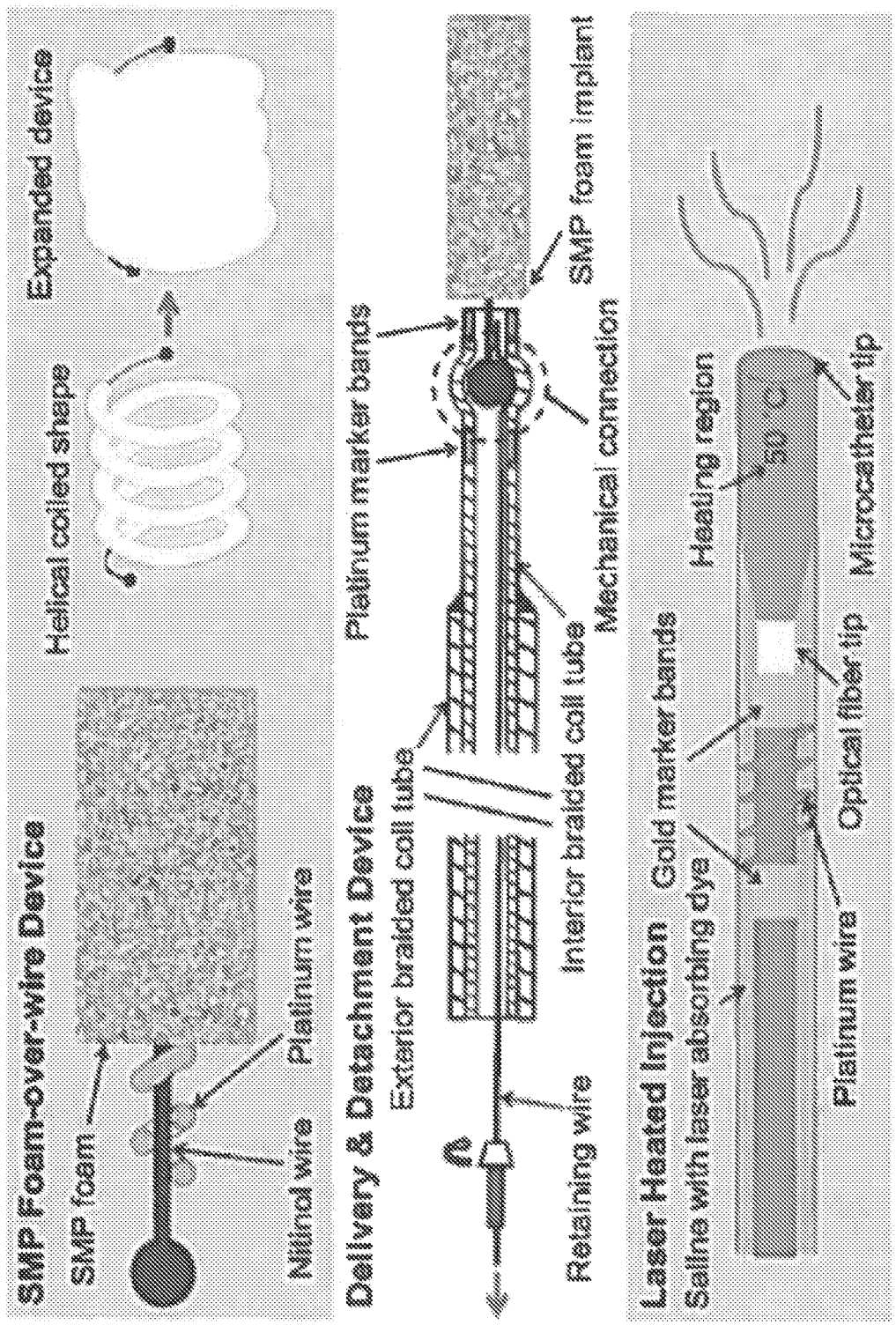
FIG. 1 is an illustration of an SMP foam-over-wire device, a delivery and detachment device, and a device for laser heated injection.

In the following description, numerous specific details are set forth but embodiments of the invention may be practiced without these specific details. Well-known circuits, structures and techniques have not been shown in detail to avoid obscuring an understanding of this description. "An embodiment", "various embodiments" and the like indicate embodiment(s) so described may include particular features, structures, or characteristics, but not every embodiment necessarily includes the particular features, structures, or characteristics. Some embodiments may have some, all, or none of the features described for other embodiments. "First", "second", "third" and the like describe a common object and indicate different instances of like objects are being referred to. Such adjectives do not imply objects so described must be in a given sequence, either temporally, spatially, in ranking, or in any other manner.

An embodiment addresses treatment of saccular aneurysms using shape memory polymer (SMP) foam to improve clinical outcomes. SMP foam-over-wire (FOW) embolization devices were delivered to in vitro and in vivo in porcine saccular aneurysm models to evaluate device efficacy, aneurysm occlusion, and acute clotting. FOW devices demonstrated effective delivery and stable implantation in vitro. In vivo porcine aneurysms were successfully occluded using FOW devices with theoretical volume occlusion values greater than 72% and rapid, stable thrombus formation. An embodiment may be used as an actuation mechanism for embolic devices.

SMP foams have been proposed to improve the healing outcomes when treating intracranial aneurysms. An embodiment addresses heating an anatomical volume with an implanted compressed SMP foam device to initiate foam expansion above body temperature. The temperature of the anatomy is increased by injecting a heated fluid volume through a catheter with an internal heating element. Heat from the fluid transfers to the compressed SMP to initiate foam expansion.

During delivery of these devices, it is desirable for the user to have control over the actuation of the device. The properties of the material can be tailored such that the transition temperature in water is higher than body temperature, preventing the device from returning to its original configuration without external stimulation. Therefore, a clinician performing the procedure will have a long working time to deliver the device without concern of passive actuation due to body heat. Once delivered, the heated injection described can be used to quickly raise the temperature around the device locally, heating it to above its transition temperature to actuate the device.

Applicant has determined an injection of heated saline (heated ex vivo) that has been described in some previous applications is not a viable option in many instances because the body acts as a heat sink and rapidly cools the injection to body temperature prior to reaching the implant site. With embodiments described herein, the injection is heated at the catheter tip, ensuring that the injection is at the desired temperature at the implant site. A novel aspect of an embodiment is injecting a solution that is heated at the distal end of the catheter via laser absorption or resistive heating that can be used to heat and actuate SMPs, shape memory alloys (SMAs), and/or SMP foams. Multiple active heating methods have been previously proposed such as magnetic, solvent, and laser coupled, but these involve directly coupling the energy source to the material, heating the material directly. In contrast, an embodiment provides a mechanism to heat the volume surrounding the implant to achieve actuation. The optical fiber tip and resistive coil designs described herein are optimized for heating the volume surrounding the implant to achieve actuation.

An embodiment describes a method to endovascularly heat an anatomical volume using a heated fluid injection, with the heating mechanism located within a catheter. The injection can be heated in at least two different ways: through the absorption of laser radiation or through conductive heating from a resistive heater. The laser radiation is delivered to the solution being injected using an optical fiber. The fiber tip couples to a centering mechanism to keep the fiber concentric with the catheter tube. Multiple embodiments of this design will be described below.

An embodiment of the laser absorption application requires that the injection absorb the laser wavelength chosen. This can be done by tailoring the laser wavelength to the injection or by adding dopants to the injection. An embodiment of the resistive heater application requires passing a current though a coiled wire, increasing the temperature of the injection surrounding the coil. Embodiments may be used to actuate SMPs and/or SMAs implanted into the body. The SMP or SMA device would be implanted, but would remain in its deformed, secondary shape until heated. Following device implantation, either the optical fiber or resistive coil would be passed through the catheter to a specified distance proximal to the catheter tip. The injection and heater would be engaged, thus heating the volume around the implant, and actuating the implant to its primary shape.

Laser Heating

Laser heating can be accomplished through various configurations. In one embodiment, laser couples into laser absorbing dye (e.g., indocyanine green), where the dye absorbs the laser radiation and heats the injection. In one embodiment, laser couples into laser absorbing particles (e.g., gold nanoparticles), where the particles absorb the laser radiation and heat the injection. In one embodiment, laser couples directly into water (wavelength optimized for water absorption), where the water in the injection absorbs the laser radiation and increases in temperature.

Fiber Tip Configurations

Fiber tips may be configured in various ways. In one embodiment, the fiber tip is a cleaved fiber tip of bare glass. In one embodiment, the fiber tip is a polymer tip attached to a glass fiber tip that allows for easier navigation as the glass edge of the glass fiber tip won't catch on the catheter wall. In one embodiment, a thermocouple is placed proximal to the fiber tip to monitor for excessive heating. In one embodiment, a thermocouple is placed distal to fiber tip on a wire extension to monitor temperature of the volume being heated.

Centering Methods

In one embodiment, radiopaque marker bands are attached to an optical fiber and wires are attached to the outside of radiopaque marker and wound around fiber from distal to proximal marker band. Wire diameter is chosen such that the combined wire diameters and optical fiber diameter are approximately equal to the catheter inner diameter.

In one embodiment, wires are attached to the optical fiber and wound around a fiber from a distal tip of the fiber to a specified distance proximal to the distal tip. A radiopaque marker is attached to bands over the wires at the distal tip and at the proximal terminus. The marker band is sized such that the outer diameter is approximately equal to the inner diameter of the catheter.

In one embodiment, a nitinol tube with an inner diameter equal to an outer diameter of optical fiber is used. The nitinol tube is laser cut and is shape set so the cut struts expand and contact the catheter wall, keeping the device centered.

Embodiments ensure the fiber tip is centered so the tip does not rest against the catheter wall. Without centering the tip could burn the catheter if the tip is against the wall as the optical energy is most intense at the fiber tip. The centering portion ensures that there is a gap between the tip and the wall and also helps ensure a more uniform heating of the injection.

Resistive Heating Methods

In one embodiment, current is passed through a high resistance wire, which heats surrounding fluid conductively. An overall device diameter of the heater should be smaller than the inner diameter of the microcatheter it is designed to pass through.

Resistive Heater Tip Configurations

In one embodiment, a high resistance wire (such as nichrome) is wound around a core wire. Wire(s) can be wound as a doublet (wire doubles back on itself) or grounded through a core wire. In one embodiment, a metal tube is wound with resistive wire(s) within a lumen of the tube. In one embodiment, resistive wires are wound around a core consisting of insulated thermocouple leads, terminated with an exposed welded junction can be incorporated into the core wires.

Heating Via Laser

After delivery of the implant, the optical fiber is delivered to the catheter tip (i.e., in an embodiment the implant is no longer located within the catheter when the heating of the fluid occurs within the catheter). In many cases, a balloon catheter proximal to the location of heating will be used to stop or lessen blood flow to minimize convective cooling at the injection site. The injection is delivered through the catheter at a specified flow rate and the laser is turned on and set to deliver a specific optical power. Depending on the laser wavelength and injection composition, the injection may or may not require a laser absorbing dopant to heat. When the laser is activated, the solution in the catheter is heated and injected to the site of interest, locally heating the environment the implant is positioned, heating it above its transition temperature and returning it to its original configuration.

The laser heated injection prototype includes a cleaved tip optical fiber with two radiopaque marker bands at a specified distance apart. Platinum wires were laser welded to the markers and wound around the fiber. An 808 nm diode laser firing at 1.9-2 W was used to heat the injection. The injection consisted of indocyanine green doped phosphate buffered saline at a concentration of 375 uM (absorption coefficient: −31 cm$^{-1}$). The injection was delivered at 1.5 ml/min and resulted in a temperature rise of 13° C.

Heating Via Resistive Heating

The resistive heating element can be fabricated in a variety of ways. For example, an insulated high resistance wire (such as nichrome) can be wound around a core wire. The wire can be wound as a doublet to facilitate current flow, or grounded through the internal core wire. Wire pitch and spacing is important to prevent recirculation zones that would lead to boiling the injection and introducing embolic air bubbles into the blood. For example, the wire wind can include gaps between adjacent winds approximately the same width as the wound wire diameter. If the outer diameter of the heater is approximately the same as the catheter inner diameter, fluid is forced through this spiraling channel. Alternatively, the wire coil can be covered with a metal tube to ensure laminar flow of the injection. The metal tube may be heated through conduction from the internal resistive wire or wires. The inner core that the resistive wires are wrapped around can be composed of one or multiple wires. For instance, the core wires can incorporate insulated thermocouple leads that are terminated with an exposed welded junction. For any device embodiment, the overall device diameter should be less than the inner lumen of the microcatheter.

The resistive heater is used in a similar way to the laser heater. The resistive coil is delivered to the catheter tip. The injection is delivered through the catheter at a specified flow rate and electrical current is passed through the leads to the resistive coil, heating the injection. The local environment around the implant is heated, actuating the implant to its original configuration.

In an embodiment the resistive heating prototype consists of an insulated nichrome wire doublet wound around a nitinol core wire and two insulated thermocouple leads. The thermocouple leads were welded together at the distal end and attached to the core wire. The proximal nichrome wire leads were fitted with adapters for a power supply. A device prototype with a resistance of 59 Ohms successfully raised the temperature of an in-vitro aneurysm model by 14° C. with a fluid injection rate of 3 ml/min and a voltage ramp of 16 to 19 volts. The injection fluid was degassed reverse osmosis water.

For either the laser or resistive heat source, it may be advantageous to use an injection fluid with a higher boiling temperature than water. Biocompatible blood substitutes with high boiling points include the perflourocarbons perfluoroperhydrophenanthrene, perfluoro-n-octane, perfluorohexane, and perfluorodecalin. It is important to degas these solutions to prevent bubbling out of solution.

Shape Memory Polymer Foam Treatment

SMPs exhibit the ability to maintain a temporary shape and subsequently recover their original shape in response to a thermal, chemical, or optical stimulus. SMPs fabricated into a foam geometry are advantageous for endovascular embolization due to their large surface area to volume ratios. This can provide scaffolding for thrombus formation and tissue healing while maintaining the ability to undergo large volume transitions required for catheter delivery and subsequent aneurysm occlusion. Polyurethane SMP foams have been reported with excellent biocompatibility and tunable thermal and mechanical properties for improved actuation control.

Previous studies investigating saccular aneurysm occlusion using SMP foam documented excellent aneurysm occlusion, mild inflammatory response, and mature tissue healing. However, these devices were designed for catheters too large for conventional neurovascular applications. Embodiments were developed to accommodate delivery with traditional microcatheters. An embodiment employs an SMP foam that is delivered to an aneurysm over a radiopaque wire backbone, mechanically detached, and then actuated either passively using physiological conditions or using a laser heated injection or resistive heated injection. Devices were fabricated and delivered to in vitro and in vivo saccular aneurysm models. Delivery and detachment efficacy, laser heating efficacy, aneurysm volume occlusion, and acute clotting were measured and evaluated during the studies.

WORKING EXAMPLES

Embolization Device Design and Fabrication

An embolization device system include an SMP FOW implant device and a cable tube delivery and detachment device with an optional laser heated saline injection for SMP foam expansion (e.g., see FIG. 1).

Shape Memory Polymer Foam-Over-Wire Implant

The SMP FOW implant device includes SMP foam secured around a platinum wound nickel-titanium (nitinol) backbone wire (e.g., see top panel of FIG. 1). SMP foam was synthesized and foamed according to known protocols 100TM composition. The 100TM composition was chosen for delayed expansion at physiologic conditions to facilitate microcatheter delivery and capability of either passive expansion at physiologic conditions or active expansion using the laser heated injection. Under sonication, 8 mm SMP foam cylinders were chemically etched in 0.1 N hydrochloric acid, cleaned using isopropyl alcohol and detergent, and then rinsed with reverse osmosis (RO) water. Cleaned foam cylinders were dried overnight in an oven at 50° C. under vacuum.

Figure 2:
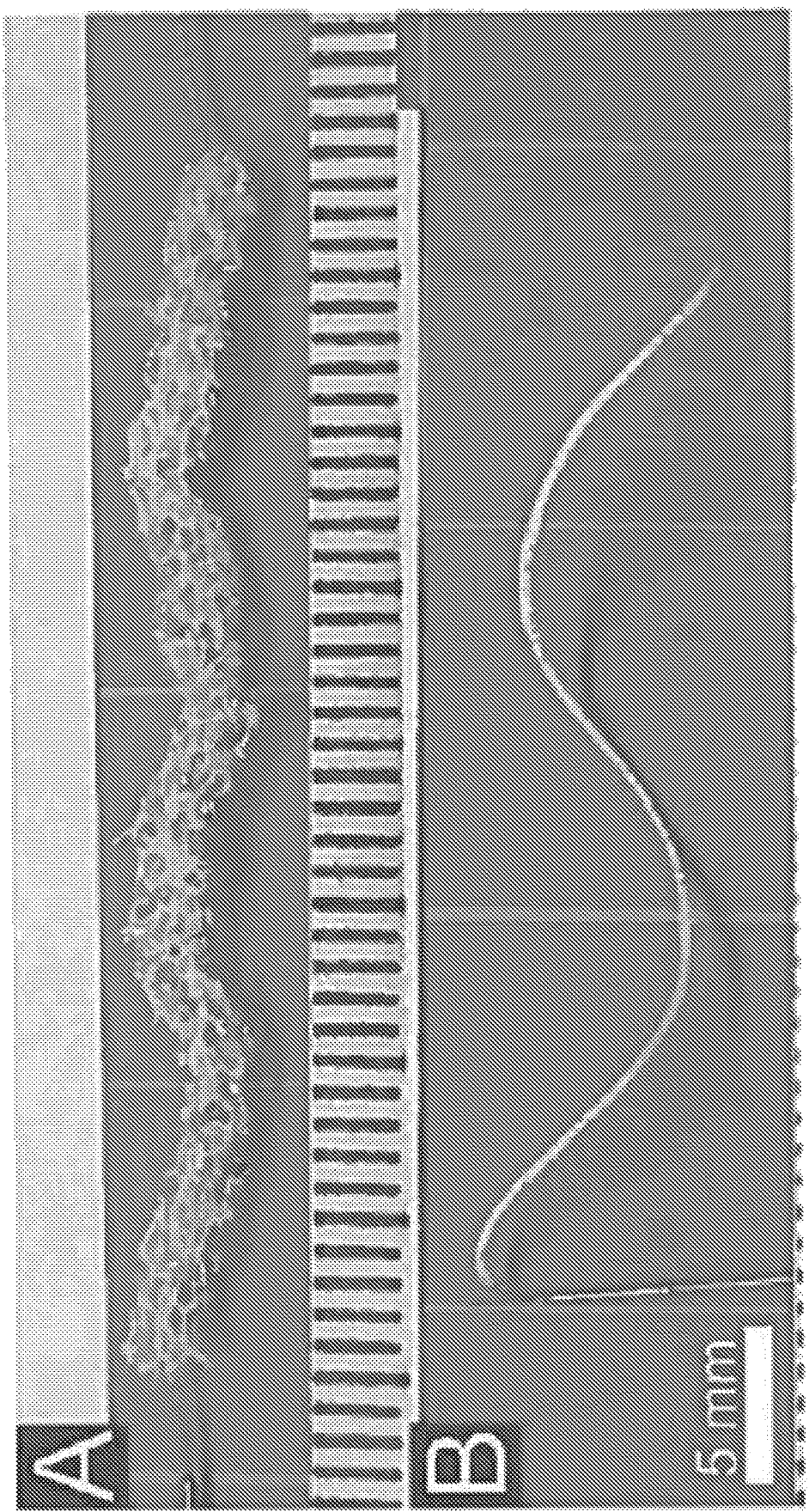
FIGS. 2A and 2B are photographs of an SMP foam cylinder in uncompressed and compressed states respectively.

The platinum-nitinol wire backbone was annealed over a mandrel in a furnace to set a helical shape, quenched in water, and cleaned using isopropyl alcohol. SMP foam cylinders of 2.5 mm diameter were cut from the cleaned and dried cylinders using a biopsy punch and the wire backbone was threaded axially through the SMP foam (e.g., see FIG. 2A). Devices were fabricated with both 2 cm and 4 cm total lengths of SMP foam. The implant devices were held taught and the SMP foam was radially compressed (FIG. 2B) using a heated SC250 Stent Crimpert. Medical grade UV-cure epoxy was used to secure the compressed SMP foam at each end of the device.

Delivery and Detachment Device

A braided coil assembly (e.g., see the middle panel of FIG. 1) includes a 0.31 mm outer diameter stainless steel ACTONE™ cable tube reinforced with a 0.46 mm outer diameter stainless steel ACTONE™ cable tube for distal flexibility and reinforced proximal pushability. A nitinol retention wire was passed through the entire length of the braided coil assembly. A laser welding system was used to secure a platinum marker band 4 mm from the distal tip of the braided coil assembly. A ball tip was created on each end of the implant using the laser welder and the ball tip was press-fit into the distal tip of the delivery system on top of the retaining wire, causing the braided coil to distend and apply a spring force on the ball tip. A second platinum marker band was laser welded at the distal tip of the delivery system to constrain the implant ball tip. The band or bands are not included in all embodiments. The assembled devices were individually sealed in a sterilized pouch with desiccant and, for the in vivo studies, sterilized by ethylene oxide and allowed to degas for 24 hours.

Laser Heater Device and Injection

Fiber optic cables were fabricated using 200/220/239 μlm core/cladding/buffer optical fiber and connectorized with 230 μm ST epoxy fiber connectors. Reinforced furcation and polytetratluoroethylene tubing segments were placed over the proximal 30 cm of the fiber. Gold marker bands were epoxied to the optical fiber at the distal tip and 2 cm proximal to the distal tip using medical grade thermal cure epoxy. Two platinum wires were laser welded to opposite sides of the marker bands and wound around the fiber. However, in other embodiments one, three, four or more wires may be used. The injected solution consisted of phosphate buffered saline doped with indocyanine green (ICG) at a concentration of 375 μM. The concentration was chosen to achieve a penetration depth of approximately 300 μm. A full schematic of the laser heated injection is shown in the bottom panel of FIG. 1.

Aneurysm Model Fabrication and Flow System

An aneurysm model consisting of a 10 mm diameter sphere embedded in the side of a 5 mm diameter cylinder was designed in CAD software, printed using a fused deposition modeling system, and smoothed using sandpaper. Sylgard 184 polydimethylsiloxane (PDMS) was cast and cured around the model, and the printed model was dissolved using a heated base bath.

Figure 3:
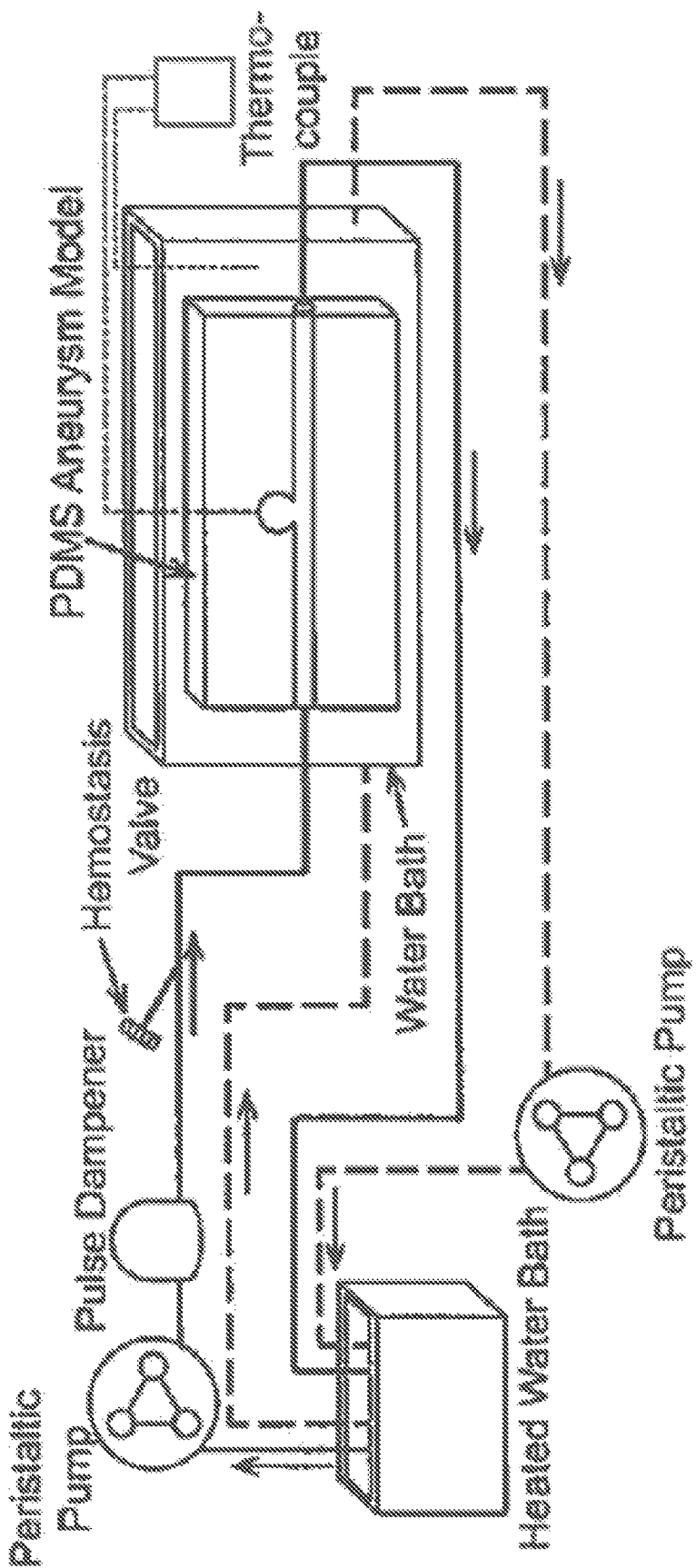
FIG. 3 is an illustration of a flow loop.

During testing, the PDMS aneurysm model was inserted in a flow loop as shown in FIG. 3. Heated RO water was siphoned into a bath with the aneurysm model to maintain isothermal conditions at 37° C. One peristaltic pump was used to maintain the water level above the submerged aneurysm model. A second peristaltic pump and pulse dampener supplied steady flow through the parent artery of the PDMS aneurysm model at approximately 240 mL/min to match the Reynold's Number of human common carotid artery peak blood flow rates. A needle thermocouple was placed through a small port at the aneurysm dome to monitor temperature during setup and removed prior to device delivery.

Embolization Device Delivery and Evaluation

Multiple FOW embolization devices were delivered via microcatheter into the aneurysm model. A 2.8/2.3 F proximal/distal microcatheter with a 0.53 mm lumen was navigated to the aneurysm using a guidewire. For each device, a hemostasis valve was used to secure a stainless steel hypotube introducer and the devices were advanced through the microcatheter to the aneurysm. Each device was positioned into the aneurysm such that the entire implant device was contained inside the aneurysm and the proximal platinum band at the distal tip of the delivery and detachment device was out of the microcatheter. The retaining wire on the delivery and detachment device was removed proximally and the cable tube was retracted into the microcatheter for complete release of the implant. The SMP foam passively actuated in the 37° C. water after implantation. Multiple devices were inserted into the aneurysm until the aneurysm was considered sufficiently occluded. Occlusion was indicated by qualitative visualization of extended dwell time or prevention of dye infiltrating the aneurysm. Theoretical volume occlusion (TVO) was calculated using Equation 1:

$$TVO = \frac{V_f}{V_a} = \frac{\pi\left(\frac{D_f}{2}\right)^2 L_f}{\frac{4}{3}\pi\left(\frac{D_a}{2}\right)^3} \qquad \text{Equation (1)}$$

where $V_f$ is expanded foam volume, $V_a$ is the aneurysm volume, $D_f$ is the expanded foam diameter, $L_f$ is the total foam length, and $D_a$ is the aneurysm diameter. The TVO calculation assumes the aneurysm is spherical and the expanded SMP foam is a uniform cylinder of 1.25 mm diameter, one-half the pre-compressed diameter, to account for foam expansion being constrained against other devices.

Laser Heater Characterization

Laser heater characterization was performed by recording the temperature of the aneurysm dome during heated injection in an in vitro flow loop similar the one shown in FIG. 3. A microcatheter was passed through a hemostasis valve to the aneurysm dome. The optical fiber was inserted through a Y-adapter hemostasis valve and the tip was positioned approximately 2 cm proximal to the distal tip of the catheter. The ICG solution was injected using a syringe pump through the Y-adapter on the microcatheter. Systemic flow was discontinued and the ICG injection was initiated at a flow rate of 1.5 mL/min. An 808 nm continuous wave diode laser was activated to emit radiation at approximately 1.9-2 W. The temperature in the dome of the aneurysm was measured every ten seconds for two minutes. Three devices were used and three injections were characterized for each device.

Porcine Sidewall Saccular Aneurysm Model Creation

Animal studies were conducted in accordance with policies set by the Texas A&M University Institutional Animal Care and Use Committee and met all federal requirements as defined in the Animal Welfare Act, the Public Health Service Policy, and the Humane Care and Use of Laboratory Animals. Additionally, studies observed NIH guidelines (or for non-U.S. residents similar national regulations) for the care and use of laboratory animals (NIH Publication #85-23 Rev. 1985).

Fluoroscopic visualization was achieved using the Allura Xper FD20 system. A saccular sidewall vein pouch aneurysm model created in a 3-4 month old 30-40 kg Yorkshire swine using a previously described model. Study subjects were premedicated with Telazol 5 mg/kg and 0.01 mg/kg buprenorphine administered intramuscularly. Following endotracheal intubation, study subjects were mechanically ventilated and maintained on isoflurane. Using sterile technique, a 10 cm incision was made in the ventral cervical midline and using a combination of sharp and blunt dissection the external jugular vein and carotid arteries were isolated. A 4 cm long segment of the external jugular vein was isolated, excised, and divided transversely to create two 2 cm open-ended pouches. The common carotid arteries were cleaned of adventitia, and vascular clamps placed at each end of the target area on the artery. A 3-4 mm arteriotomy was created and an end-to-side anastomosis of the venous pouch to the carotid artery performed using 7-0 polypropylene sutures. A 6-9 mm diameter aneurysm was created on each common carotid artery of two animals for a total of four aneurysms. After hemostasis was confirmed, the subcutaneous tissues were loosely closed.

Embolization Device Delivery and Angiographic Evaluation

Each aneurysm was accessed via endovascular technique for device delivery and implantation. A 6 F intravascular sheath was inserted percutaneously into the femoral artery with ultrasound guidance and a 5 F guide catheter was inserted through the introducer. Using fluoroscopic guidance, the guide catheter was advanced over a guidewire to the proximal right or left carotid artery proximal to the aneurysm. Digital subtraction angiography with 3-D reconstruction angiography was performed to fully characterize each aneurysm. A 2.8/2.3 F proximal/distal microcatheter with 0.53 mm lumen was navigated to the aneurysm using a guidewire. Multiple FOW embolization devices were delivered through microcatheters and deployed in each aneurysm under fluoroscopic guidance. Devices were delivered and detached using the same methods used during in vitro studies. After implantation, the SMP foam passively expanded in the physiological conditions. Additional devices were inserted into the aneurysm until the aneurysm was considered sufficiently occluded. Adequacy of occlusion was determined qualitatively by visualization of extended dwell time or prevention of dye infiltrating the aneurysm. TVO was calculated using Equation 1, where $D_a$ was the aneurysm diameter averaged from four measurements taken from angiographic images obtained using various angles, with the same assumptions as conducted for in vitro studies.

Laser Heated Injection

The laser heated injection was used in one aneurysm after implantation with FOW devices to accelerate and increase expansion of the SMP foam. The laser heating device was positioned using the same methods used during in vitro studies. A second 6 F introducer was inserted into the femoral artery on the opposite side of the previous introducer. A 5 F balloon catheter was inserted through the second introducer and positioned proximal to the aneurysm site adjacent to the guide catheter. The balloon catheter was inflated to prevent blood flow to the aneurysm and ICG-doped saline was injected at 1.5 mL/min through the microcatheter. The same laser used for in vitro studies was activated for 2 minutes during injection. After injection, the balloon catheter was deflated and angiography was performed to confirm aneurysm integrity and assess any change in aneurysm occlusion.

Ex Vivo Evaluation

After implantation and angiographic imaging of both aneurysms in each animal, the animal was sacrificed and the aneurysms explanted and rinsed in saline. The parent artery was divided axially and the aneurysm neck was exposed and imaged. The aneurysm wall was opened and the implanted devices were imaged within the aneurysm sac and after removal from the aneurysm to evaluate implant device stability, aneurysm occlusion, and clotting.

Results

Embolization Device Delivery

Figure 4:
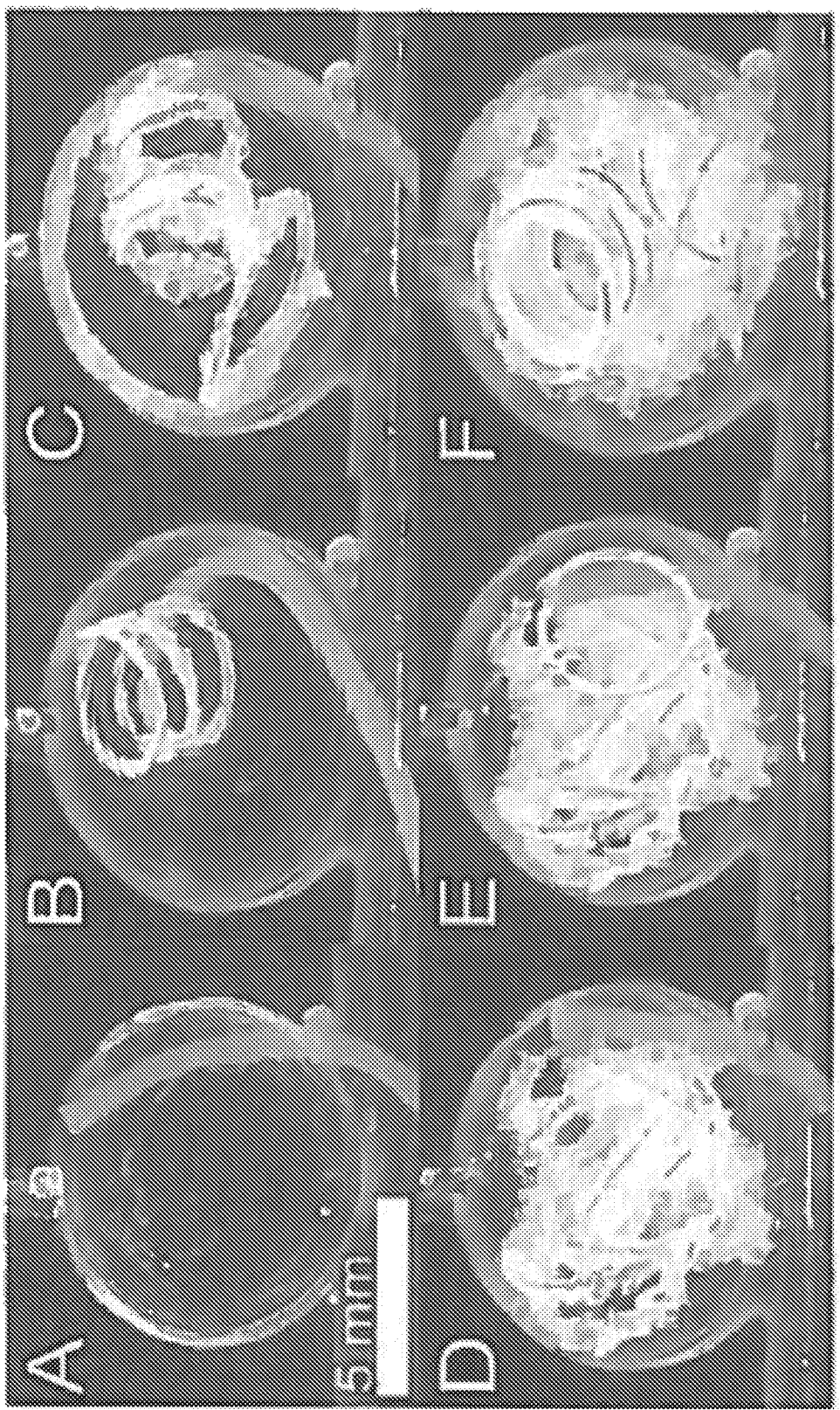
FIG. 4 is a collection of photographs illustrating embolization-device delivery into an aneurysm model.

The spherical aneurysm model was fabricated with a dome diameter of 9.79±0.12 mm and a neck diameter ranging 2.09-6.81 mm. Embolization device delivery into the aneurysm model is shown in FIG. 4. Four FOW devices 4 cm in length were delivered to the aneurysm model. Two of four implant devices were detached without complication, whereas two devices detached in the microcatheter during repositioning and were successfully deployed using a guidewire. All four devices were implanted into the aneurysm model without migration into the parent vessel. TVO was calculated to be 40%.

Laser Heater Characterization

The conducted in vitro tests showed that three of the tested devices increased the aneurysm dome temperature to at least 49° C. after 1-1.5 minutes of injection.

Embolization Device Delivery and Angiographic Evaluation

Figure 6:
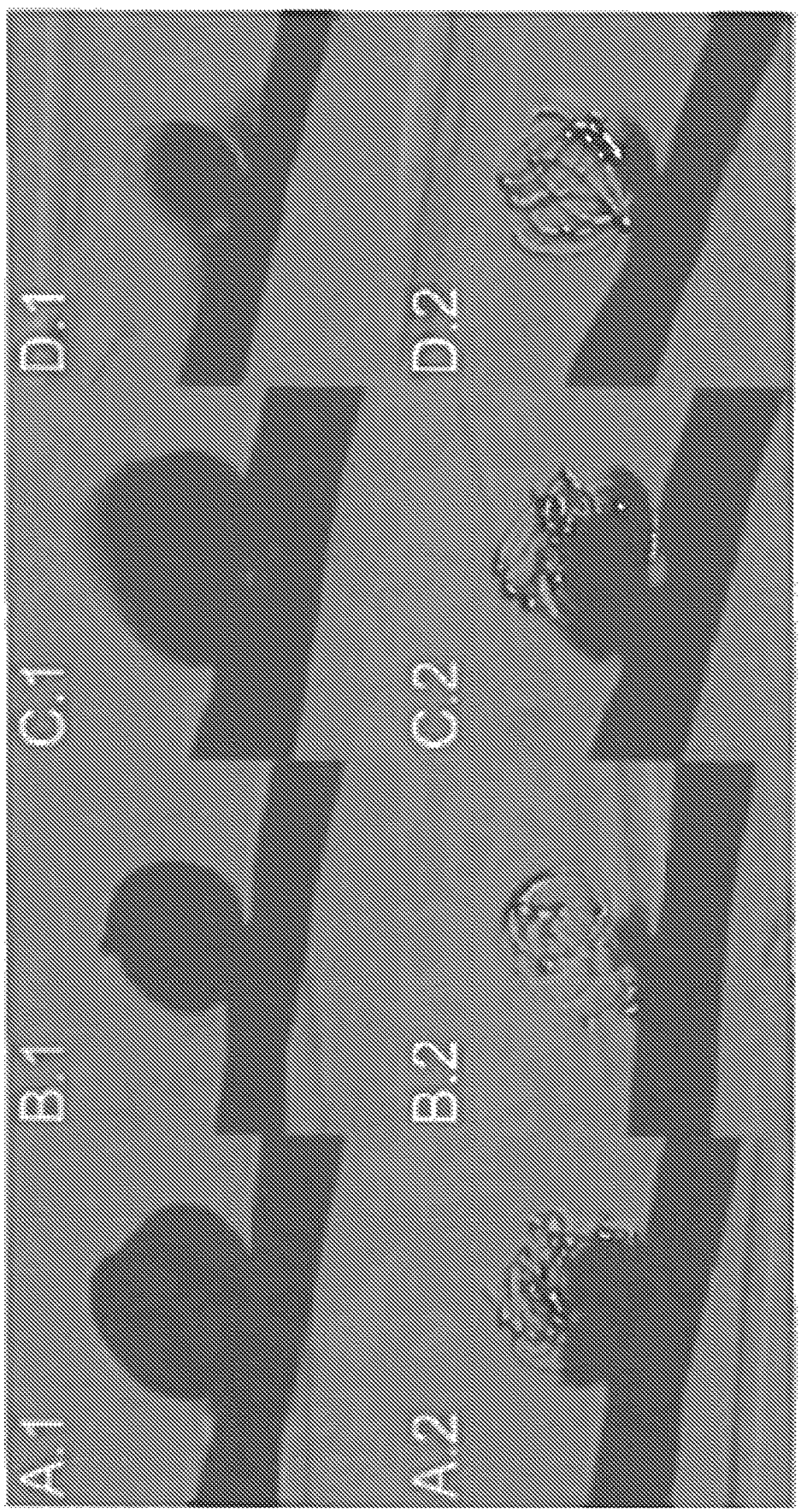
FIG. 6 illustrates angiographic evaluation of aneurysms before and after treatment.

After aneurysm formation, three of four aneurysms exhibited good stability via angiography, while one aneurysm showed hemorrhage at the anastomosis site. All four aneurysms were successfully treated with FOW embolization devices. FIG. 6 summarizes angiographic evaluation of each aneurysm before and after treatment. All treated aneurysms exhibited significant occlusion, particularly at the dome apex, with reduced contrast infiltration into the aneurysm. Hemorrhage at the anastomosis site shown in panel 0.1 is no longer seen after treatment as shown in panel D.2. The minimal TVO calculated for the four aneurysms was 72% (Table 1).

Figure 7:
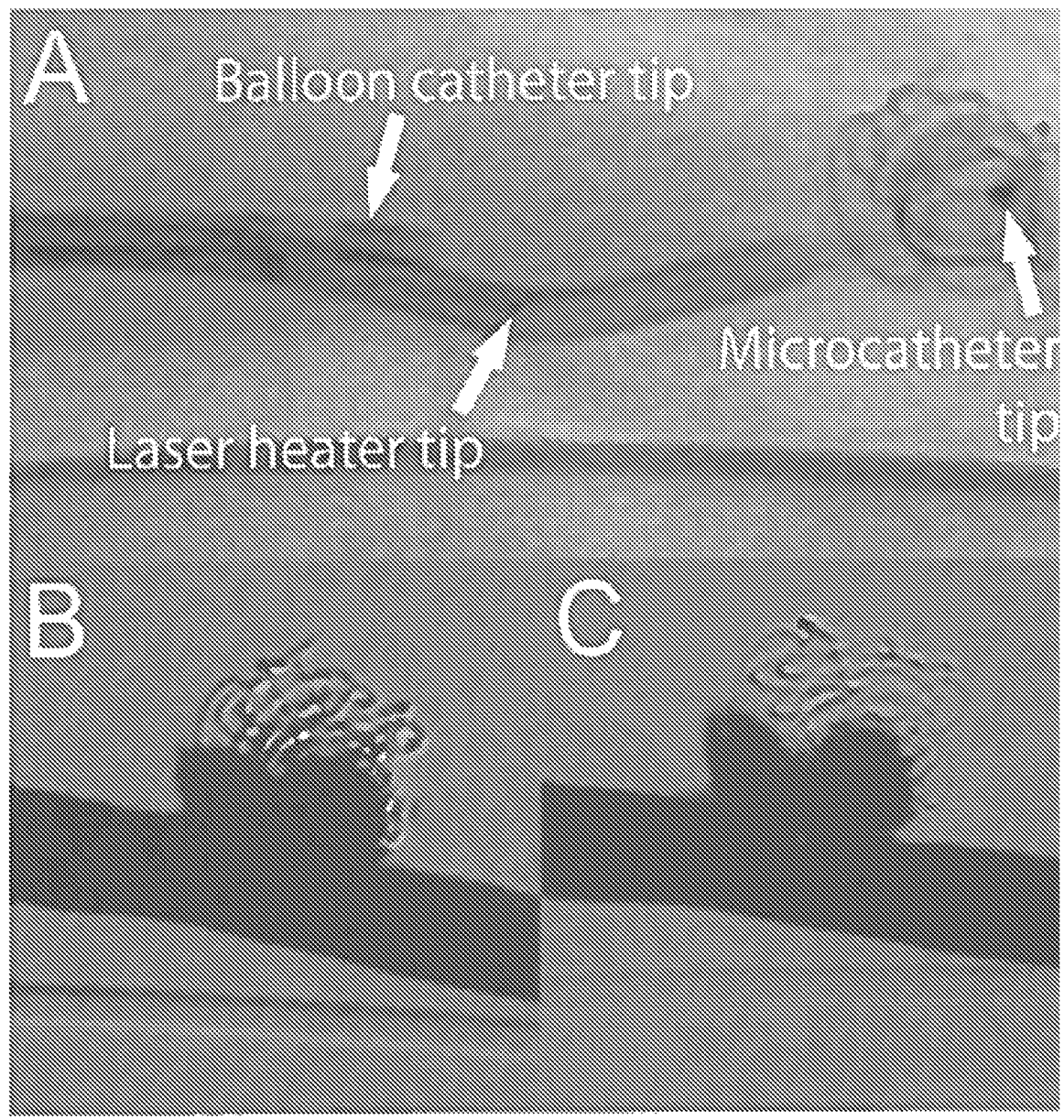
FIG. 7 is a collection of photographs illustrating laser-heated injection.

Embolization devices were delivered and implanted in the aneurysms with minimal complications. All device components were clearly identified under fluoroscopy. 19 of 26 (73%) FOW devices inserted into the microcatheter were successfully implanted in aneurysms, two devices could not be packed into aneurysms that had already occluded, and five devices could not be advanced due to excessive device expansion within the catheter. Delivery and detachment of devices was successfully performed in 24 of 26 (92%) attempts with both complications being detachment of the implant during repositioning. One detached device was delivered to the aneurysm using a guidewire and the other was partially packed in the aneurysm and subsequently removed using an endovascular snare system. As shown in FIG. 7, the laser heated injection was conducted without complication and no acute adverse reactions were detected. Minimal reduction in contrast infiltration was observed following the laser heated injection.

Ex Vivo Evaluation

Figure 8:
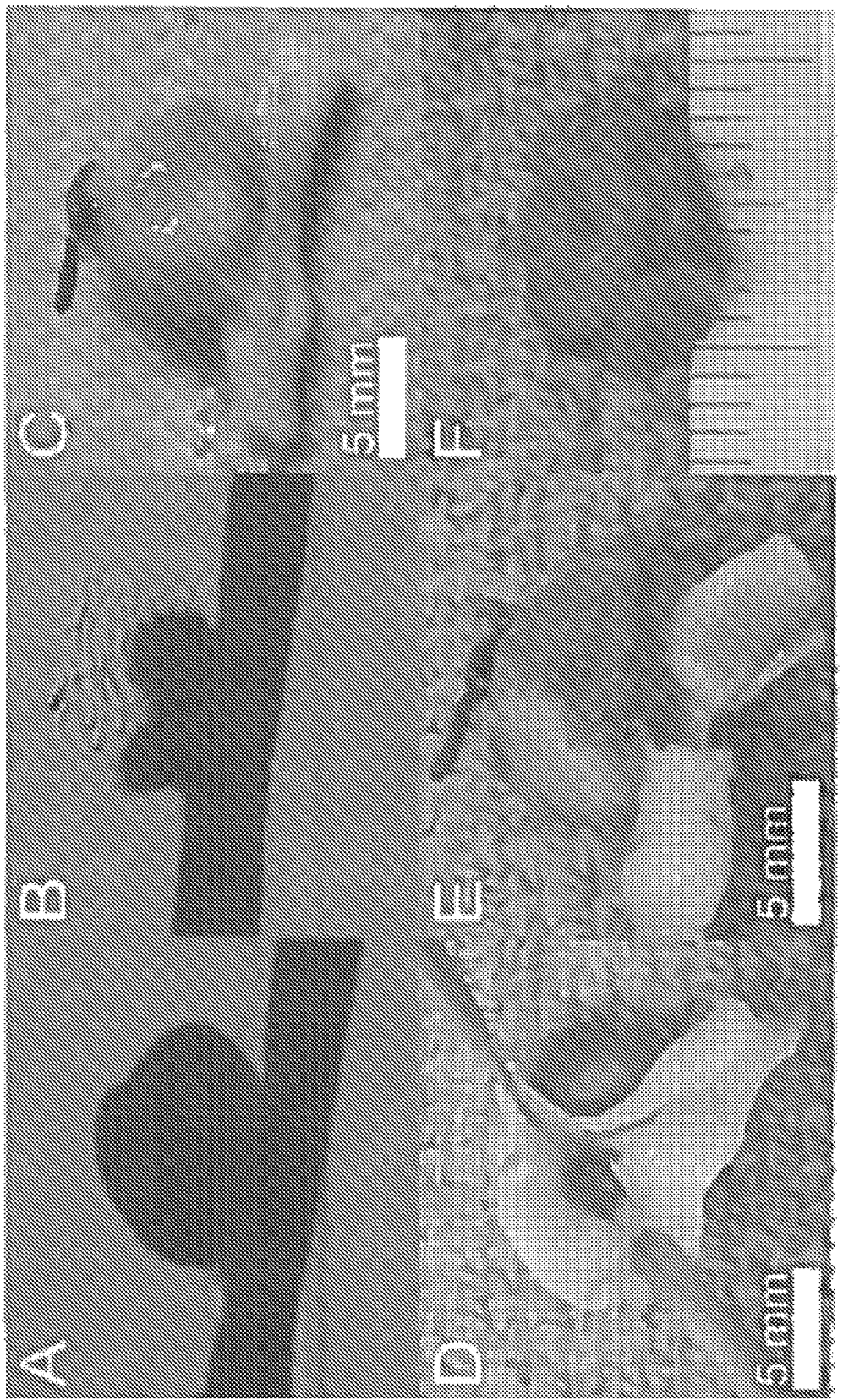
FIG. 8 is a collection of photographs illustrating an explanted aneurysm and the aneurysm content of implanted devices and thrombus.

The explanted aneurysms showed no device perforation through the aneurysm wall and excellent thrombus formation throughout the implanted FOW devices. FIG. 8 shows an explanted aneurysm and the aneurysm content of implanted devices and thrombus. All aneurysms were explanted within 3 hours after final device implantation in each aneurysm.

Discussion

The primary goal of these studies was to evaluate the efficacy of FOW embolization devices for endovascular treatment of saccular aneurysms. The devices were tested using in vitro and in vivo saccular aneurysm models to measure and evaluate delivery and detachment efficacy, laser heating efficacy, aneurysm volume occlusion, and acute clotting.

The embolization device delivery in vitro demonstrated excellent positioning of multiple devices in the saccular aneurysm model with no device protrusion or migration into the parent vessel (FIG. 4). The device detachment success rate of 50% revealed a need for increased grip strength and consistency in fabrication, both of which were implemented for devices fabricated for the in vivo study. TVO of the in vitro study was lower than expected due to limited total device length of 16 cm relative to the large aneurysm diameter, but still resulted in greater than reported volume occlusion values for bare platinum coil treatments. Furthermore, the TVO assumption of 1.25 mm SMP foam expanded diameter is a conservative estimate relative to published shape recovery values of greater than 80% at physiologic conditions.

Figure 5:
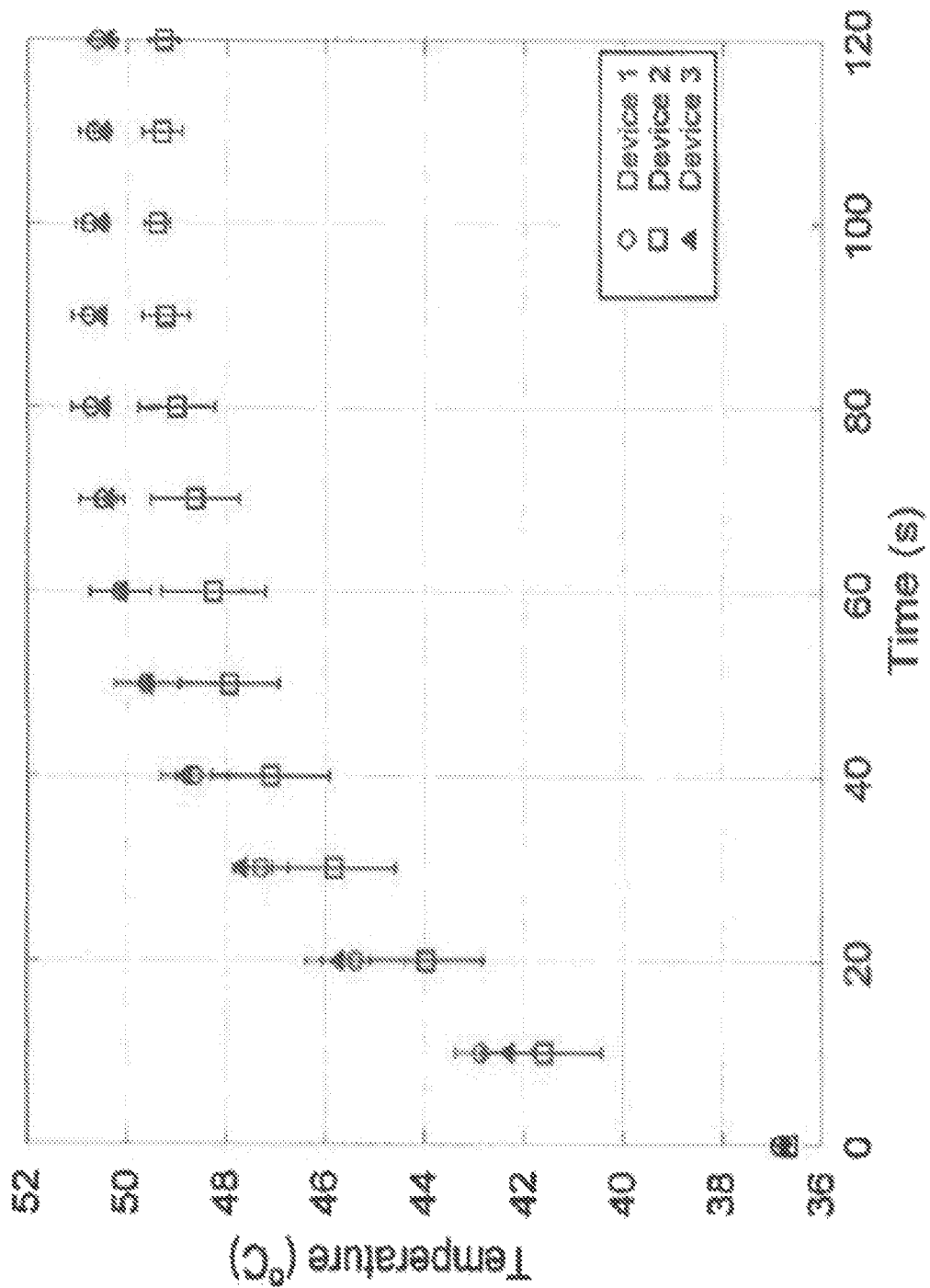
FIG. 5 illustrates the increase in temperature in the aneurysm dome during in vitro studies due to a laser heated microcatheter injection.

All three laser heating devices increased the temperature (e.g., see FIG. 5) in the aneurysm dome during in vitro studies to a temperature 10° C. greater than the published SMP foam transition temperature for successful SMP foam actuation. Heating profile variation could be due to device imperfections or variation in the connector alignment and fiber tip location in the catheter.

Post treatment angiography during the in vivo study shown in FIG. 6 exhibited complete elimination of flow into the aneurysm dome apex and substantial reduction of flow near the aneurysm neck in all 4 aneurysm models. The porous structure and low radiographic contrast of the SMP foam enables contrast agent to infiltrate the foam and be visualized under fluoroscopy. Therefore, the absence of contrast agent flow into the aneurysm indicates complete thrombus formation within the implanted SMP foam. This is drastically different compared to treatments with bare platinum coils that saturate the aneurysm space with radiographic contrast and prevent visualization of any infiltrating contrast agent. In those cases, occlusion by thrombus formation cannot be reliably assessed in vivo. Thrombus formation within the porcine aneurysm models was confirmed by evaluation of the explanted aneurysms as shown in FIG. 8. All aneurysm contents exhibited stable thrombus formation throughout the implant device mass. The formation of stable thrombus is an early and critical step in the inflammation response that has been shown to promote fibrous connective tissue formation within implanted SMP foams, resulting in stable occlusion. The thrombus formation throughout the explanted aneurysm mass also suggests that flow penetrating into two of the four treated aneurysms is an artifact of the 2D imaging overlaying flow around the outside of the ball of implanted contents.

Embolization devices were implanted with stable positioning of multiple devices in each saccular aneurysm model. Implant devices had a moderate success rate with complications of increased delivery friction due to foam expansion in the microcatheter indicating a need for increased foam hydrophobicity to delay passive expansion. Detachment devices were able to deliver, reposition, and retract almost all devices without complication. The two detachment device complications were the direct result of either a fully packed aneurysm preventing device delivery or undesired SMP foam expansion and can be addressed without a detachment design change. The laser heating injection resulted in minimal decrease of contrast infiltration in the treated aneurysm, indicating either complete passive expansion of SMP foams or that the temperature increase was not sufficient to increase SMP foam expansion. However, no negative acute effects were observed as a result of the laser heating. As shown in Table 1 below, TVO of the in vivo study was excellent in all cases with values higher than those published using bare platinum coils (23-37%) and equal or greater to published values for HydroCoil® devices (45-73%). However, the aneurysm D value (Table 1) may be falsely high due to angiography measurements underestimating the actual diameter of the aneurysm possibly due to incomplete contrast filling due to the anastomosis hemorrhage of aneurysm D (FIG. 6 D.1) before treatment.

TABLE 1

Aneurysm model and device dimensions and TVO values

| Aneurysm Label | Aneurysm Diameter (mm) | Neck Diameter (mm) | No. Devices | Total device Length (cm) | Theoretical Volume Occlusion |
|---|---|---|---|---|---|
| A | 8.66 ± 1.45 | 4.42 | 6 | 20.0 | 72% |
| B | 7.45 ± 1.11 | 4.63 | 4 | 16.1 | 91% |
| C | 7.78 ± 1.91 | 4.42 | 6 | 14.9 | 74% |
| D | 5.74 ± 0.77 | 3.4 | 3 | 11.4 | 141% |

In conclusion, the FOW embolization device design combines the filling and surface area advantages of SMP foam with fluoroscopic contrast and mechanical stability of metal coils, providing a low adoption hurdle for clinicians experienced with bare metal coil devices. Furthermore, the in vitro and in vivo studies show great promise for the efficacy of the FOW embolization device for endovascular treatment of intracranial saccular aneurysms.

Embodiments cover the application of embolic foams delivered to cerebrovascular aneurysms, but these endovascular injection heaters can be used for other SMP foam embolic devices for other embolic applications. Further, such heating solutions are not limited to SMP foams but may be used with other occlusion devices that actuate based on heat.

ADDITIONAL EXAMPLES

Example 1 includes a system for delivery via a microcatheter, the system comprising an SMP foam that is adapted to be delivered to backbone desired vascular anatomy, detached therefrom, and then actuated either passively using physiological conditions, using a laser heated injection, or resistively heated injection.

Example 2 includes the system of example 1, wherein, for either the laser or resistive heat sources, an injection fluid with a higher boiling temperature than water is used to absorb heat in an area proximate to the SMP foam to heat the SMP foam above a transition temperature of the SMP foam.

Example 3 includes the system of example 1, wherein laser heating comprises a laser absorbing dye that is positioned proximate to the SMP foam, and wherein the laser absorbing dye is adapted to absorb heat from a laser to heat the injection.

Example 4 includes the system of example 1, wherein laser heating comprises laser absorbing particles that are positioned proximate to the SMP foam, and wherein the laser absorbing particles are adapted to absorb heat from a laser to heat the injection.

Example 5 includes the system of example 1, comprising a fiber tip, wherein the fiber tip is one of a cleaved fiber tip of bare glass, a polymer tip attached to a glass fiber tip.

Example 6 includes the system of example 1, comprising a thermocouple to monitor heating of the injected fluid volume, the SMP foam or an area surrounding the SMP foam.

Example 7 includes a method of endovascularly activating an SMP foam, the method comprising: delivering an implant comprising the SMP foam to an implant site via a catheter; delivering an optical fiber to the implant site via the catheter; delivering an injection fluid to the implant site via the catheter; directing a laser towards the implant site to heat the injection within the catheter or within a volume in proximity to the SMP foam to heat the SMP above its transition temperature.

Example 8 includes the method of example 7, wherein the injection comprises at least one of a laser absorbing particle or a laser absorbing dye.

Example 9 includes the method of example 7, wherein the injection fluid has a higher boiling temperature than water.

Example 10 includes a method of endovascularly activating an SMP foam, the method comprising: delivering an implant comprising the SMP foam to an implant site via a catheter; delivering a resistive wire to the implant site via the catheter; delivering an injection fluid to the implant site via the catheter; passing electrical current through the resistive wire to heat the injection in an area proximate to the SMP foam to heat the SMP foam above its transition temperature.

Example 11 includes the method of example 10, wherein the resistive wire comprises an insulated nichrome wire doublet that is wound around a core wire and two insulated thermocouple leads.

Example 12 includes a kit comprising an optic fiber that heats an injection directly within the catheter using the optic fiber tip. Instead of heating the SMP foam directly, an embodiment heats a solution, which then heats the foam.

Example 13 includes a kit comprising a resistive heater that heats an injection directly within the catheter using the resistive heater. Instead of heating the SMP foam directly, an embodiment heats a solution, which then heats the foam.

Applicant determined laser embodiments may be advantageous as they heat the solution volumetrically (volumetric absorption of the laser radiation by the solution within the catheter), rather than by conductively heating the fluid in direct contact with the resistive heater. Heating volumetrically reduces the likelihood of developing local hotspots where one may accidentally boil the injection, resulting in bubble formation. However, Applicant further determined resistive heaters may be more cost effective than laser heaters and are viable if one mitigates boiling. Using injection fluids with higher boiling temperature than water helps alleviate hot spots, which can lead to boiling.

Example 1b includes a system comprising: a catheter; an optic fiber having a long axis and a short axis that is orthogonal to the long axis; first and second radiopaque elements coupled to the optic fiber; a first wire coupled to the optic fiber and extending from the first radiopaque element to the second radiopaque element; a fluid; wherein (a)(i) the first wire wraps at least partially around an exterior surface of the optic fiber; (a)(ii) an outer diameter of the first wire and an outer diameter of the optic fiber are collectively less than an inner diameter of the catheter, and (a)(iii) the first wire is configured to center the optic fiber within the catheter within a plane orthogonal to the long axis.

For instance, in FIG. 9A catheter 901 couples to radiopaque elements 902, 903 and first wire 905. The cross-sectional view of FIG. 9A shows two additional wires.

The system may be included in a kit. The kit may include the catheter or may not. The kit may include the fluid or may not. For instance, a hospital may purchase the heating system but may use its own catheter and/or fluid (e.g., saline). The system may include only one radiopaque element in some embodiments. In some embodiments, the first wire may be radiopaque and couple to bands that are not radiopaque with the idea being that the first wire provides centering regardless of how it couples to the optic fiber.

Example 2b includes the system of example 1b wherein the fluid includes at least one member selected from the group comprising a perfluorocarbon.

Example 3b includes the system of example 2b wherein the perfluorocarbon includes at least one member selected from the group comprising perfluoroperhydrophenanthrene, perfluoro-n-octane, perfluorohexane, and perfluorodecalin.

Example 4b includes the system of example 1b wherein the fluid has a higher boiling temperature than water.

Example 4c includes the system of example 1b wherein the fluid includes a saline solution.

Example 5b includes the system of example 1b wherein the fluid includes at least one member selected from the group comprising a laser absorbing particle and a laser absorbing dye.

Example 6b includes the system of example 1b wherein the plane intersects both the first wire and the first radiopaque element.

For instance, this occurs as location 904.

Example 7b includes the system of example 6b wherein the first radiopaque element is between the first wire and the optic fiber.

For example, this occurs at location 904.

Example 8b includes the system of example 1b including a shape memory polymer (SMP) foam coupled to a shape memory alloy (SMA).

Example 9b includes the system of example 8b, wherein the system is configured such that (b)(i) in a first configuration the plane intersects a distal portion of the catheter, the SMP foam, and the SMA and in a second configuration the plane intersects the distal portion of the catheter and a distal portion of the optic fiber, and (b)(ii) the optic cable is not coupled to the SMP foam.

For instance, the system is configured to work sequentially whereby a SMP foam is advanced through the catheter and then out into an aneurysm or physical anomaly. Afterwards, the heating system is advanced within the catheter to heat the fluid. The heated fluid then flows out of the catheter and into the aneurysm or physical anomaly to actuate the SMP foam.

Example 10b includes the system of example 1b comprising a polymer coupled to an exterior surface of a distal end portion of the optic fiber, wherein the polymer is not monolithic with the optic fiber.

For example, see polymer tip 907 of FIG. 9C.

Example 11b includes the system of example 1b comprising a thermocouple, wherein a plane orthogonal to the long axis intersects both the optic fiber and the thermocouple.

For example, see thermocouple 906 of FIG. 9C.

Example 12b includes the system of example 11b wherein a distal tip of the thermocouple is proximal to a distal tip of the optic fiber to monitor the catheter volume temperature to prevent overheating.

For example, see FIG. 9C.

Example 12c includes the system of example 11b wherein a distal tip of the thermocouple is proximal to a distal tip of the optic fiber.

Example 13b includes the system of example 10b wherein a distal tip of the thermocouple is distal to a distal tip of the optic fiber to monitor the anatomy volume temperature to prevent overheating.

For example, see FIG. 9D.

Example 13c includes the system of example 10b wherein a distal tip of the thermocouple is distal to a distal tip of the optic.

Example 14b includes the system of example 1b comprising: a second wire coupled to the optic fiber and extending from the first radiopaque element to the second radiopaque element; wherein (b)(i) the second wire wraps at least partially around the exterior surface of the optic fiber; (a)(ii) the first and second wires are collectively configured to center the optic fiber within the catheter within the plane; and (a)(iii) the plane intersects the first and second wires and the optic fiber.

For example, see the cross-sectional view of FIG. 9A. Increasing the number of wires may promote better centering. Centering of an optic fiber may be key in ensuring the highest energy is directed towards fluid that is linearly aligned with a long axis of a distal portion of the catheter. For instance, a physician using the marker bands would know the optic fiber is heating fluid directly aligned with the line coupling the marker bands (as opposed to a non-centered tip that could be heating fluid off at an angle to the tip of the catheter).

Example 15b includes a system comprising: a catheter; an optic fiber having a long axis and a short axis that is orthogonal to the long axis; a metal conduit fixedly coupled to the optic fiber; fluid; wherein (a)(i) a plane orthogonal to the long axis intersects both the optic fiber and the metal conduit, (a)(ii) in a first configuration the metal conduit has a first maximum outer diameter measured orthogonal to the long axis and in a second configuration the metal conduit has a second maximum outer diameter measured orthogonal to the long axis, (a)(iii) the second maximum outer diameter is greater than the first maximum outer diameter but smaller than an inner diameter of the catheter, and (a)(iv) the metal conduit is configured, when in the second configuration, to center the optic fiber within the catheter and in the plane.

For instance, see FIGS. 9E and 9F and conduit 908 coupled to optic fiber 901.

Example 16b includes the system of example 15b wherein the metal conduit includes a shape memory alloy (SMA).

Example 17b includes the system of example 16b wherein the system is configured such that (b)(i) in an additional first configuration the plane intersects a distal portion of the catheter, the SMP foam, and the SMA and in an additional second configuration the plane intersects the distal portion of the catheter and a distal portion of the optic fiber, (b)(ii) the optic cable is not coupled to the SMP foam, and (b)(iii) the metal conduit includes a plurality of slots that in the first configuration extend orthogonal to the short axis.

For instance, see slot 909 of FIG. 9E. Also, this again connotes a sequence of deployment whereby the foam is implanted and then the heater system warms fluid in the catheter and the fluid then exits the catheter and heats the foam to actuate the foam.

Example 18b includes a system comprising: a catheter; a coiled wire comprising (a)(i) a long axis orthogonal to a short axis, and (a)(ii) two leads configured to couple to opposite poles of an energy source; a thermocouple; a fluid; a shape memory polymer (SMP) foam coupled to a shape memory alloy (SMA); wherein the system is configured such that (b)(i) in a first configuration a plane orthogonal to the long axis intersects a distal portion of the catheter, the SMP foam, and the SMA and in a second configuration the plane intersects the distal portion of the catheter and a distal portion of the coiled wire; and (b)(ii) the coiled wire is not coupled to the SMP foam.

Figure 10A:
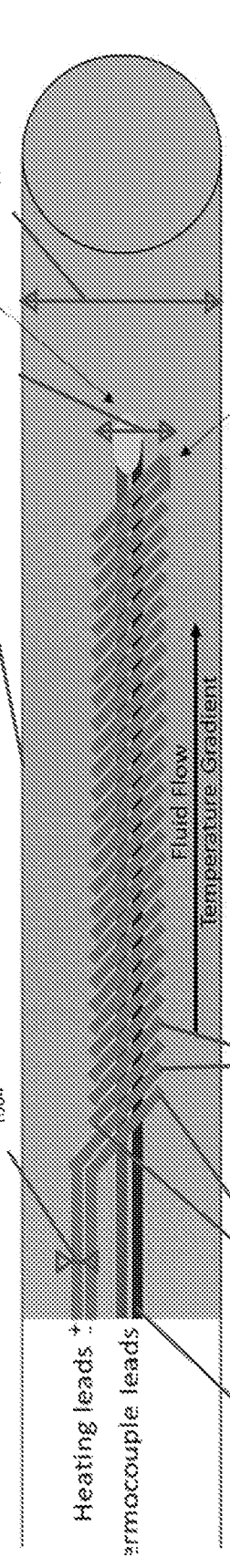
FIGS. 10(A)-(C) include differing embodiments of a resistance heated actuation system.

For instance, see FIG. 10A. The coiled wire includes a doublet having an outgoing wire portion 1002 and returning wire portion 1003. The diameter of the coiled wire 1006 is about 50% of the diameter of the catheter 1007. The pitch is tight and is less than the diameter 1004 of a lead. Thermocouple 1001 is within the coiled heating wire.

The coiled wire may coil around a middle substrate, such as a rod or other wire. This rod or other wire may include a thermocouple wire system or may be in addition to such a thermocouple wire system. This substrate is not depicted in FIG. 10A. For example, the substrate may include a SMA (e.g., nitinol).

Some embodiments may use a unipolar heating coil.

Example 19b includes the system of example 18b comprising a metal conduit, wherein: the plane intersects the metal conduit and the coiled wire; in the second configuration the system is configured to pass the fluid between the metal conduit and the catheter.

Example 19c includes the system of example 18b comprising a metal conduit, wherein: the plane intersects the metal conduit and the coiled wire; in the second configuration the system is configured to pass the fluid between the metal conduit (i.e., outside the metal conduit) and the catheter.

For instance, see conduit 1008. The conduit may include a SMA. Fluid may flow outside the conduit. The flow may be laminar based on the smooth form factor of the conduit. This reduced flow eddies. The conduit itself heats and then heats fluid.

Example 20b includes the system of example 18b wherein an outer diameter of the coiled wire is less than 90% of an inner diameter of the catheter.

For instance see FIG. 10A and diameters 1006 and 1007.

Example 21b includes the system of example 18b wherein an outer diameter of the coiled wire is more than 95% of an inner diameter of the catheter and is configured to center the coiled wire within the catheter.

Figure 10B:
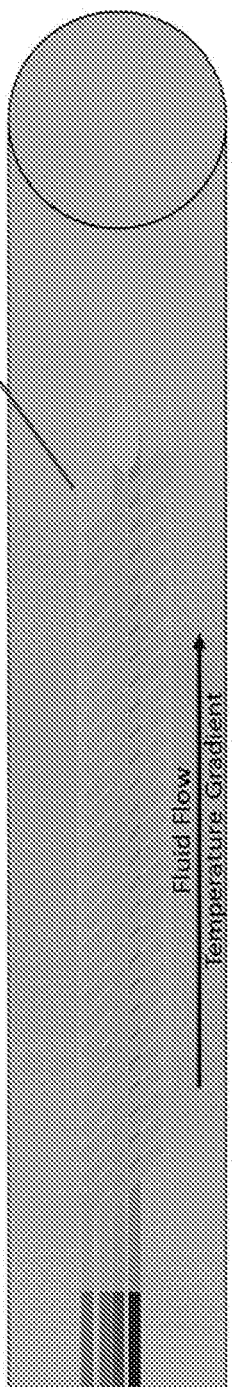
Figure 10C:
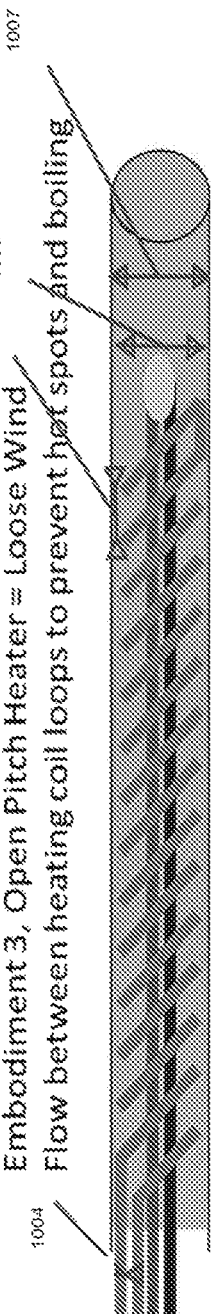

For instance see FIG. 10C and diameters 1006 and 1007.

Example 22b includes the system of example 21b wherein one of the two leads has a first outer diameter and a pitch between two adjacent coiled portions of the coiled wire is greater than 95% of the first outer diameter.

For instance, see pitch 1009 of FIG. 10C based on diameter 1004 of a lead. Pitch 1009 is much larger than diameter 1004. The large diameter 1006 limits flow between the coiled heating element and the catheter wall, forcing fluid flow in a spiral pattern along the wire winds. This forced convection due to the large pitch and large diameter helps avoid focal fluid boiling due to hot spots and recirculation zones.

Above embodiments have repeatedly referenced resistive heating and optic fiber heating. However, other embodiments may include other forms of heating such as radiofrequency (RF) heating and the like. For example, instead of the coiled resistive heating elements of FIG. 10A-C the coiled wire may be substituted with an RF heating element.

While the claimed invention has certain preferred embodiments, it will be obvious to those skilled in the art that various changes and modifications may be made therein without departing from the invention, and all such changes and modifications are intended to fall within the true spirit and scope of the invention.

What is claimed is:

1. A system comprising:
   a catheter;
   an optic fiber having a long axis and a short axis that is orthogonal to the long axis;
   first and second radiopaque elements coupled to the optic fiber;
   a first wire coupled to the optic fiber and extending from the first radiopaque element to the second radiopaque element;
   a second wire coupled to the optic fiber and extending from the first radiopaque element to the second radiopaque element; and
   a fluid;

wherein (a)(i) the first wire wraps at least partially around an exterior surface of the optic fiber; and (a)(ii) an outer diameter of the first wire and an outer diameter of the optic fiber are collectively less than an inner diameter of the catheter;

wherein (b)(i) the second wire wraps at least partially around the exterior surface of the optic fiber; (b)(ii) the first and second wires are collectively configured to center the optic fiber within the catheter within a plane orthogonal to the long axis; and (b)(iii) the plane intersects the first and second wires and the optic fiber.

2. The system of claim 1 wherein the fluid includes a perfluorocarbon.

3. The system of claim 2 wherein the perfluorocarbon includes at least one of perfluoroperhydrophenanthrene, perfluoro-n-octane, perfluorohexane, perfluorodecalin, or combinations thereof.

4. The system of claim 1 wherein the fluid has a higher boiling temperature than water.

5. The system of claim 1 wherein the fluid includes at least one of a laser absorbing particle, a laser absorbing dye, or combinations thereof.

6. The system of claim 1 wherein the plane intersects both the first wire and the first radiopaque element.

7. The system of claim 6 wherein the first radiopaque element is between the first wire and the optic fiber.

8. The system of claim 1 including a shape memory polymer (SMP) foam coupled to a shape memory alloy (SMA).

9. The system of claim 8, wherein the system is configured such that (b)(i) in a first configuration the plane intersects a distal portion of the catheter, the SMP foam, and the SMA and in a second configuration the plane intersects the distal portion of the catheter and a distal portion of the optic fiber, and (b)(ii) the optic wire is not coupled to the SMP foam.

10. The system of claim 1 comprising a polymer coupled to an exterior surface of a distal end portion of the optic fiber, wherein the polymer is not monolithic with the optic fiber.

11. The system of claim 1 comprising a thermocouple.

12. The system of claim 11 wherein a distal tip of the thermocouple is proximal to a distal tip of the optic fiber.

13. The system of claim 11 wherein a distal tip of the thermocouple is distal to a distal tip of the optic fiber.

14. A system comprising:
a catheter;
an optic fiber having a long axis and a short axis that is orthogonal to the long axis;
first and second radiopaque elements coupled to the optic fiber;
a wire coupled to the optic fiber and extending from the first radiopaque element to the second radiopaque element;
a fluid including a perfluorocarbon;
wherein (a)(i) the wire wraps at least partially around an exterior surface of the optic fiber; (a)(ii) an outer diameter of the wire and an outer diameter of the optic fiber are collectively less than an inner diameter of the catheter, and (a)(iii) the wire is configured to center the optic fiber within the catheter within a plane orthogonal to the long axis.

15. The system of claim 14 wherein the perfluorocarbon includes at least one of perfluoroperhydrophenanthrene, perfluoro-n-octane, perfluorohexane, perfluorodecalin, or combinations thereof.

16. The system of claim 14 wherein the fluid has at least one of (a) a higher boiling temperature than water, (b) a laser absorbing material, or (c) combinations thereof.

17. A system comprising:
a catheter;
an optic fiber having a long axis and a short axis that is orthogonal to the long axis;
first and second radiopaque elements coupled to the optic fiber;
a wire coupled to the optic fiber and extending from the first radiopaque element to the second radiopaque element;
a thermocouple; and
a fluid;
wherein (a) the wire wraps at least partially around an exterior surface of the optic fiber;
(b) an outer diameter of the wire and an outer diameter of the optic fiber are collectively less than an inner diameter of the catheter, (c) the wire is configured to center the optic fiber within the catheter within a plane orthogonal to the long axis.

18. The system of claim 17 wherein the fluid has a higher boiling temperature than water.

19. The system of claim 17 wherein a distal tip of the thermocouple is proximal to a distal tip of the optic fiber.

20. The system of claim 17 wherein a distal tip of the thermocouple is distal to a distal tip of the optic fiber.

* * * * *